United States Patent [19]

Shiraishi

[11] Patent Number: 4,574,042

[45] Date of Patent: Mar. 4, 1986

[54] GAS ANALYZING APPARATUS

[75] Inventor: Hideo Shiraishi, Yokohama, Japan

[73] Assignee: Fuji Electric Corporate Research & Development Co., Ltd., Yokosuka, Japan

[21] Appl. No.: 576,636

[22] Filed: Feb. 3, 1984

[30] Foreign Application Priority Data

Feb. 14, 1983 [JP] Japan .................................. 58-21727

[51] Int. Cl.[4] .......................................... G01N 27/46
[52] U.S. Cl. ..................................... 204/429; 204/426
[58] Field of Search ........................ 204/1 S, 421-429

[56] References Cited

U.S. PATENT DOCUMENTS

| | | | |
|---|---|---|---|
| 3,907,657 | 9/1975 | Heijne et al. ........................ | 204/427 |
| 3,940,327 | 2/1976 | Wagner et al. ...................... | 204/426 |
| 3,989,614 | 11/1976 | Tien ..................................... | 204/426 |
| 4,121,989 | 10/1978 | Shum et al. .......................... | 204/426 |
| 4,272,331 | 6/1981 | Hetrick ................................ | 204/425 |
| 4,292,158 | 9/1981 | Muller et al. ........................ | 204/429 |
| 4,464,244 | 8/1984 | Uchida et al. ....................... | 204/424 |

Primary Examiner—T. Tung
Attorney, Agent, or Firm—Brumbaugh, Graves, Donohue & Raymond

[57] ABSTRACT

In the particular embodiments of the invention described in the specification, a gas analyzer for determining the oxygen content of a gaseous mixture has a ceramic substrate formed with a cavity at one end which is covered by a zirconia electrolyte disc. A small aperture admits gas to the cavity. The zirconia disc has electrodes coated on opposite sides and the ceramic substrate has strip conductors leading from the cavity to terminate at the opposite end.

5 Claims, 5 Drawing Figures

GAS ANALYZING APPARATUS

BACKGROUND OF THE INVENTION

This invention relates to a gas analyzing apparatus of the type mounted in automobiles and the like and, more particularly to a gas analyzing apparatus which may be used as a highly reliable oxygen meter, particularly as an oxygen shortage monitor.

In order to improve combustion efficiency of automobile engines and to make exhaust gases less harmful, a lean burn combustion type engine has been developed in which use is made of a lean air-fuel ratio. In such engines the weight ratio of air to fuel is higher than the theoretical air-fuel ratio of 14.7. However, oxygen sensors or air-fuel ratio meters heretofore in use for measuring the theoretical air-fuel ratio are not precise in terms of their electromotive force output when used in a lean atmosphere and therefore it is impossible for such sensors to precisely measure or detect the air-fuel ratio for a lean mixture. For this reason, various types of apparatus are installed on the intake side of a lean burn engine to keep the lean atmosphere approximately constant so as to provide good combustion control. The disadvantage of such apparatus is that this method of control not only makes the mixture control apparatus expensive but also prevents highly accurate control because of its low response speed.

Since the air-fuel ratio i.e., the weight ratio of air to fuel, can be determined by measuring the oxygen content of the mixture, gas analyzing cells constructed to measure the oxygen content through a sampling method have been proposed. The theoretical construction of such a gas analyzing cell is shown in FIG. 1. In the gas analyzing cell shown in FIG. 1, the gas to be analyzed is first introduced into a gas analyzing compartment 12 through a coupling means 10 and subsequently withdrawn from the compartment. In this case, the coupling means 10 is constructed of, for instance, an opening highly resistant to gas diffusion. Moreover, the oxygen is withdrawn by means of a partition 16 composed of an oxygen ion conductor forming part of a wall 14 of the gas analyzing compartment. The amount of electric charge required to be applied to the partition 16 for withdrawing the oxygen may be used as an index of the content of the oxygen. For this purpose, the partition 16 has a pair of electrodes 18 and 18' for detecting temperature, a pair of pressure sensing electrodes 20 and 20', and a pair of oxygen withdrawing electrodes 22 and 22'. Each of the electrodes 18, 18', 20, 20', 22 and 22' is connected by a conductor 24 to the outside of the device.

An object of the present invention is to provide a gas analyzing apparatus of the above type especially suitable for use in automobiles and having improved strength and reliability.

SUMMARY OF THE INVENTION

In accordance with the present invention a gas analyzing apparatus of the above type includes a cell with a gas analyzing compartment formed at one end of an insulating ceramic substrate and metal conductors coated on the ceramic substrate to connect electrodes in the gas analyzing compartment to the outside of the cell. In other words, according to the present invention, a gas analyzying cell having oxygen withdrawing action is formed at one end of an insulating ceramic substrate and conductive film strips connected to each electrode of the cell are affixed to the surface of the ceramic substrate and extend to the other end thereof so that the cell and its conductors are incorporated in the ceramic substrate, providing a gas analyzing apparatus having excellent strength and improved reliability which can easily be handled.

In a preferred embodiment, the gas analyzing compartment located at one end of an elongated alumina ceramic substrate is formed with grooves consisting of concentric circles having different diameters, the circular grooves being made by a multistage form extending transverse to the thickness of the substrate and an aperture is made in the substrate portion in which the circular grooves are formed and a solid zirconia electrolytic disc is mounted in the circular grooves.

Moreover, it is also preferred that the main part of each of the metal strip conductors is formed of a platinum strip one end of which is connected to an external electrode of the solid zirconia electrolytic disc through a platinum wire, the other end being joined with a thick platinum film containing glass frit and connected to a terminal. In addition, it is also preferred that the surfaces of the external electrodes of the solid zirconia electrolytic disc and the platinum strips on the substrate are provided with a ceramic coating.

BRIEF DESCRIPTION OF THE DRAWINGS

Exemplary embodiments of the present invention will be described in detail hereinafter with reference to the accompanying drawings, in which.

DESCRIPTION OF PREFERRED EMBODIMENTS

Figure 2:
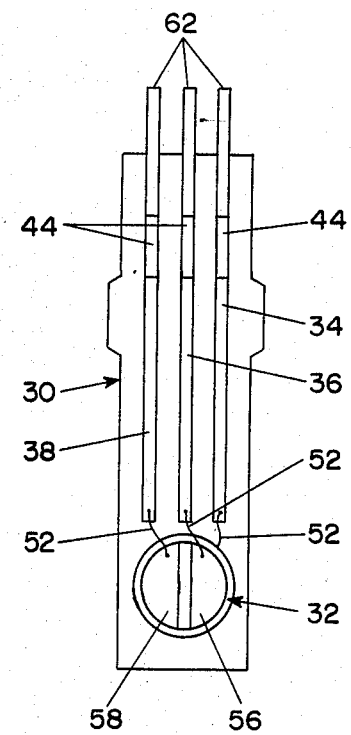
FIG. 2 is a vertical view of a representative embodiment of a gas analyzing apparatus in accordance with the present invention with the ceramic coating 60 removed.
Figure 3:
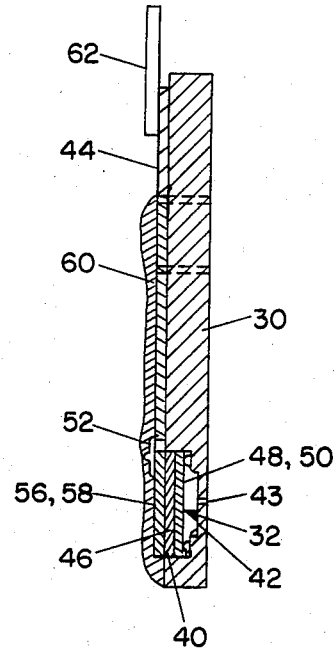
FIG. 3 is a vertical sectional view of the gas analyzing apparatus shown in FIG. 2.

In the representative embodiment of the invention shown in FIGS. 2 and 3, a rectangular sheet of ceramic substrate 30 is formed at one end with a gas analyzing cell 32 having an oxygen withdrawing action and three precious metal film strips 34, 36 and 38 connected to electrodes provided in the cell 32 are coated on the surface of the substrate 30 and extend to the other end of the substrate.

The substrate 30 is made of insulating alumina or the like which is formed in a rectangular shape, pressed and baked. Two circular grooves 40 and 42 comprising concentric circles having different diameters are formed at one end of the substrate, the circular grooves being impressed by multistage forms during the pressing and baking of the substrate. In addition, an aperture 43 of about 10 μm diameter which is concentric with the circular grooves 40 and 42 is made, for example, by means of a YAG laser. Subsequently, several strip patterns 34, 36, 38 and 44 of platinum paste and glass frit (borosilicate glass) containing platinum paste are printed on one side of the substrate 30 as shown in FIG. 2 and dried. The printed pattern is then baked at 1,300° C. providing thick platinum strips containing glass frit bound to the substrate 30.

A solid zirconia electrolytic disc 46 is inserted and loosely mounted in the circular groove 40 provided near one end of the substrate 30. The reason for loosely mounting the disc 46 in the circular groove 40 is to allow for the difference in the coefficients of expansion of the materials and to enable a platinum wire to be connected to an electrode on the enclosed side of the disc. The solid zirconia electrolytic disc 46 can be prepared by baking and sintering stabilized zirconia material ($Y_2O_3$ Stabilized 6 mol %) manufactured by Zircar Products, Inc. of Florida, New York, at 1,550° C. for two hours. Two internal electrodes 48 and 50 about 1 $\mu$m thick are formed on one side of the solid zirconia electrolytic disc 46 by platinum sputtering. A platinum wire 52 is welded to one of the internal electrodes 48 and 50 by means of parallel gap spot welding and the disc is then inserted into the circular groove 40.

Figure 1:
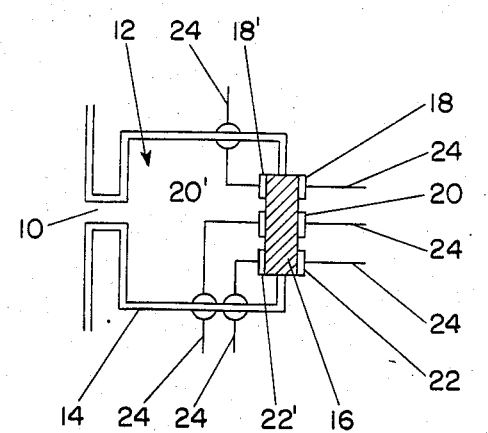
FIG. 1 is a schematic sectional view for the purpose of illustrating the principles on which a gas analyzing cell determines the content of oxygen in a sample of gas.
Figure 4:
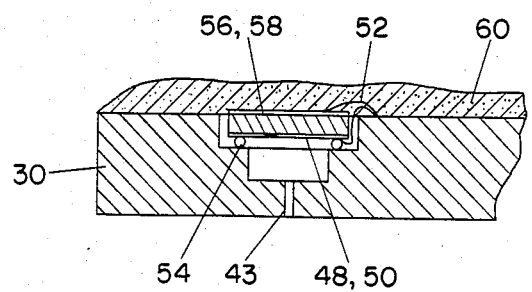
FIG. 4 is an enlarged cross sectional view of the principal portion of the apparatus shown in FIG. 3.

After the solid zirconia electrolytic disc 46 has been inserted into the substrate 30, the disc is sealed to the substrate. In this case, a hermetic seal with strong bonding strength is formed between the ceramic materials by inserting a platinum O-ring 54 between them as shown in FIG. 4 and applying a pressure of 65 MPa to the disc and substrate at a temperature of 1,010° C. for 60 minutes. After the disc has been sealed to the substrate, two external electrodes 56 and 58 are formed on the disc by platinum sputtering and the internal electrodes 48 and 50 and external electrodes 56 and 58 are welded to the thick platinum strips 34, 36 and 38 by parallel gap spot welding, using platinum wires 52. Electrode 56 is the external oxygen partial pressure sensing electrode and Electrode 58 is the external oxygen withdrawal electrode. These electrodes are paired with the internal electrodes 48 and 50 in their operation. Because the leads of the internal electrodes 48 and 50 are used together in this embodiment, they are electrically connected through the platinum O-ring 54 and joined by one of the wires 52 to the thick platinum strip 34 which provides a common conductor. In this exemplary embodiment, the electrodes corresponding to the temperature detection electrodes 18 and 18' shown in FIG. 1 are omitted. However, if such temperature detection electrodes are desired, they may be included and would have the same construction as the partial pressure sensing and oxygen withdrawing electrodes.

After the platinum wires 52 have been connected as described above, a magnesia spinel plasma (e.g. MgO-$Al_2O_3$) is sputtered onto the external electrodes 56 and 58 and the thick platinum strips 34, 36 and 38, forming a porous ceramic coating 60, about 100 $\mu$m thick, to protect them. Finally, a terminal 62 is soldered in a reducing atmosphere to the end of each platinum strip containing glass frit 44 to complete the structure providing a gas analyzing apparatus (see FIG. 2 and FIG. 3). To use the gas analyzer thus constructed, appropriate electrical connections are made to the terminals 62.

As is evident from the foregoing description the invention provides a gas analyzing cell which is formed at one end of a rectangular insulating ceramic substrate and an output signal produced by the cell is transmitted through thick platinum strips extending along the surface of the substrate to the other end so that the cell and the conducting strips are both incorporated on the one and same ceramic substrate. This results in a rugged, highly reliable gas analyzer. Moreover, in making the analyzer it is only necessary to insert a solid zirconia electrolytic disc in a circular groove in the ceramic substrate and to seal it in place. Since the cell is thereby incorporated in the substrate, it is firmly held in place, permitting convenient handling of the element.

Furthermore, the conducting strips connected to the cell are affixed on the surface of the ceramic substrate containing the cell. Consequently, it is not possible for the conductors to be disconnected and separated from the cell. The ceramic coating applied to the element protects the external electrode on the disc and the thick platinum strips from gas erosion and effectively contributes to an improvement in the reliability of the element. Accordingly, a gas analyzing apparatus assembled by mounting the element thus constructed on a desired metal housing or the like can suitably be used as an oxygen sensor, or air-fuel meter, installed in automobiles or the like.

Figure 5:
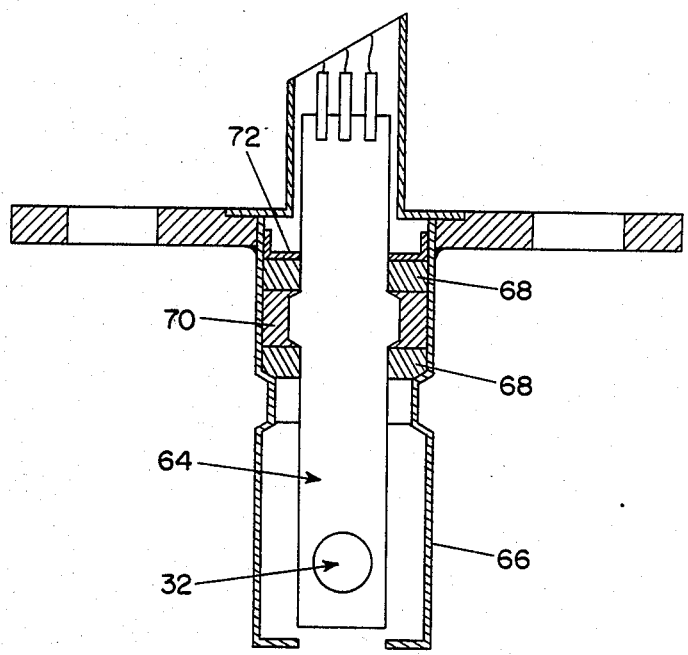
FIG. 5 is a diagrammatic cross-sectional view showing the gas analyzing apparatus of FIG. 2 in a typical installation.

FIG. 5 illustrates a representative embodiment in which the above-described element is mounted on a metal housing to provide an oxygen sensor in accordance with a particular application. As shown in FIG. 5, the element 64 is mounted on a lower metal housing 66 through an insulating collar 68 and a body of powdered material 70. The mounting can be accomplished by inserting the powdered material under pressure to form the body 70. Subsequently, a cap 72 is securely welded to the metal housing 66 by spot welding to hold an insulating collar 68 and the body of powdered material 70 and then a flange and other components are welded thereto to complete the installation of the oxygen sensor.

Although the invention has been described with reference to specific preferred embodiments, it is apparent that the invention is not limited to the described embodiments and includes modifications and alterations. For example, in the above-described exemplary embodiments, although an aperture is provided in the ceramic substrate, an aperture may instead be made in the center of the solid zirconia electrolytic disc in place of the aperture in the ceramic substrate. In this case, it is preferable not to apply any ceramic coating or else to omit the coating in the region containing the aperture. Moreover, a ceramic coating may be unnecessary, depending on the field of application.

In addition, the solid zirconia electrolytic disc may not have to be inserted into a cavity in the ceramic substrate. In that case, the circular groove for receiving the solid zirconia electrolytic disc is unnecessary and only one circular groove, to provide a compartment or chamber on one side of the solid zirconia electrolytic disc is required, the solid zirconia electrolytic disc being mounted on the surface of the ceramic substrate.

In addition, a heater circuit using conductive strips and a temperature detection circuit may be formed on the rear surface of the ceramic substrate, if necessary. In this case, the terminals 62 may be mounted on both the front and rear surfaces of the ceramic substrate.

I claim:
1. A gas analyzing apparatus comprising:
a planar insulating ceramic substrate having multistage grooves in a major surface thereof forming a cavity and a relatively small aperture extending from a surface of the substrate to an interior surface of the cavity;
an electrolytic disc mounted within the grooves so that the cavity is closed to form a gas analyzing compartment, wherein when the apparatus is placed in a region having an oxygen containing gaseous mixture to be analyzed, the gas analyzing compartment is in communication with the region through the aperture such that the gaseous mixture diffuses into the gas analyzing chamber at a relatively slow rate;

at least one pair of metallic electrodes formed on opposing major surfaces of the electrolytic disc, the electrodes being formed in a manner so as to allow any oxygen in the gas analyzing compartment to contact at least a portion of the major surface of the electrolytic disc within the gas analyzing compartment and to allow any oxygen withdrawn through the electrolytic disc to pass through at least a portion of the other major surface thereof;

means for coupling at least one pair of the electrodes to a source of electrical charge, wherein the oxygen content of the gaseous mixture is determined by the quantity of electrical charge supplied to the electrodes coupled to the source of electrical charge.

2. The gas analyzing apparatus as defined in claim 1, wherein the coupling means includes at least two metal strip conductors formed on the major surface of the substrate and electrically connected to the pair of electrodes, wherein the strip conductors each extend from the one pair of electrodes to respective terminals adjacent an edge of the substrate.

3. A gas analyzing apparatus as claimed in claim 2 wherein the cavity is formed by providing circular grooves in the substrate consisting of concentric circles having different diameters, the circular grooves being formed by a multistage mold in the direction of the thickness of the substrate, the substrate portion in which the circular grooves are provided having the aperture, and a solid zirconia electrolytic disc mounted in one of the circular grooves.

4. A gas analyzing apparatus as claimed in claim 3, wherein the main part of each of the strip conductors is formed of a platinum strip, one end of which is connected to a respective electrode of the solid zirconia electrolytic disc through a platinum wire, the other end comprising a platinum strip containing glass frit and connected to one of said terminals.

5. A gas analyzing apparatus as claimed in claim 4, wherein the surfaces of the platinum strips and the electrodes on the major surface of the zirconia disc outside of the gas analyzing compartment are covered with a ceramic coating.

* * * * *